United States Patent
Petersen

(10) Patent No.: US 6,627,207 B1
(45) Date of Patent: Sep. 30, 2003

(54) WATER-BASED, QUICK-DRYING, GEL-TYPE DISINFECTANT HAVING LOW ALCOHOL CONTENT

(75) Inventor: Jorgen Lorenzo Petersen, Hellerup (DK)

(73) Assignee: Pro-Ren A/S, Gentofte (DK)

(*) Notice: Subject to any disclaimer, the term of this patent is extended or adjusted under 35 U.S.C. 154(b) by 0 days.

(21) Appl. No.: 09/623,028

(22) PCT Filed: Feb. 26, 1999

(86) PCT No.: PCT/DK99/00091
§ 371 (c)(1),
(2), (4) Date: Oct. 11, 2000

(87) PCT Pub. No.: WO99/43205
PCT Pub. Date: Sep. 2, 1999

(30) Foreign Application Priority Data

Feb. 26, 1998 (DK) .......................... 1998 00257

(51) Int. Cl.[7] .................. A01N 25/00; A01N 25/34; A61K 6/00; A61K 7/00
(52) U.S. Cl. ................... 424/405; 424/401; 424/404
(58) Field of Search ....................... 424/401, 404, 424/405, 76.1; 510/130, 131, 132, 138

(56) References Cited

U.S. PATENT DOCUMENTS

| | | | |
|---|---|---|---|
| 5,326,492 A | 7/1994 | Hodam, Jr. ............... | 510/383 |
| 5,474,776 A | * 12/1995 | Koyanagi et al. ........... | 424/401 |
| 5,908,619 A | * 6/1999 | Scholz ..................... | 424/78.08 |

FOREIGN PATENT DOCUMENTS

| | | |
|---|---|---|
| EP | A223681 | 5/1987 |
| EP | 00437900 | 12/1990 |
| EP | A604848 | 7/1994 |
| WO | WO 93/24101 | * 12/1993 |
| WO | WO 9700667 | 1/1997 |
| WO | WO 9700668 | 1/1997 |
| WO | 9801110 | 1/1998 |
| WO | 9802137 | 1/1998 |

* cited by examiner

Primary Examiner—Thurman K. Page
Assistant Examiner—Todd D Ware
(74) Attorney, Agent, or Firm—Birch, Stewart, Kolasch & Birch, LLP

(57) ABSTRACT

A water-based, quick-drying, gel-type disinfectant composition comprising one of more anti-microbicidal ingredients, 0–30% of an alcohol, a thickening agent, an emulsifier, and water. The composition is especially relevant for use as a hand or skin disinfectant to be used in the food industry or in hospitals. The thickening agent is a crucial part of the composition and is typically selected from acrylic acid copolymers, methacrylic acid copolymers, sodium carboxycellulose, hydroxyethylcellulose, and hydroxypropylcellulose. A typical composition comprises 0.05–5.0% of a fatty alcohol-polyglycol ether as an emulsifier, 0.5–5.0% of glycerin, 0.01–2.0% of one of more additives including 0.05–1.0% of a basic compound, and substantially the balance of water.

10 Claims, 2 Drawing Sheets

WATER-BASED, QUICK-DRYING, GEL-TYPE DISINFECTANT HAVING LOW ALCOHOL CONTENT

This application is the national phase under 35 U.S.C. §371 of PCT International Application No. PCT/DK99/00091 which has an International filing date of Feb. 26, 1999, which designated the United States of America.

FIELD OF THE INVENTION

The present invention relates to quick-drying, gel-type disinfectant compositions having a surprisingly low content of alcohol. Such disinfectants have special interest in the field of hand and skin disinfection.

BACKGROUND OF THE INVENTION

For a long period, there has been a major interest for the disinfection of hands and skin in hospitals and in the food industry. In some instances, the doctors, nurses, and workers must apply a disinfectant to their hands or skin several times (20 times or more) a day. As such disinfectants should preferably result in an instantaneous removal or inactivation of micro-organisms and at the same time rapidly evaporate or become absorbed into the skin within one minute, high amounts of an alcohol, typically ethanol, are often utilised in such disinfectants as ethanol readily evaporates from the skin at body temperature. An example of a commercial high-alcohol disinfectant comprises around 60% ethanol, around 8% lanolin, around 4% of an emulsifier, and around 28% of water.

Alcohol-solution disinfectants have, thus, found broad use by doctors and nurses in hospitals and workers in the food industry. However, due to the low viscosity of such products, spillage easily occur when the disinfectant is applied to the palm of the hand and rubbed into the hand and fingers by the user. Needless to say that overflow of an alcohol-solution disinfectant is highly undesirable, and, thus, gel-type disinfectants have recently been developed.

From EP 0604848 A2 a quick-drying, gel-type disinfectant is known. The disinfectants disclosed therein typically have an alcohol content of 40–90% and further include an anti-microbicial agent, a carboxyvinyl polymer, and a water-soluble, high molecular cellulose compound as thickening agent.

A high amount of ethanol may however result in the drying out of the skin. Thus, in the food industry, this has been a major problem in the situations where the workers need to disinfect their hands numerous times a day. Frequent use of conventional high-alcohol disinfectants have in some cases led to early pensioning off workers due to permanent irritation and drying out of the skin. This problem has partly been solved in EP 0604848 A2 by using a wetting agent. However, to the best of knowledge of the present applicant, the problems associated with irritation and drying out of the skin have not been fully solved.

BRIEF DESCRIPTION OF THE INVENTION

The problem underlying the present invention is to provide disinfectant compositions which have a reduced tendency to dry out the skin of the users while at the same time having a drying time (absorption/evaporation time) of at the most a minute, preferable at the most 45 seconds, as longer drying times either would require the inconvenient use of towels or would lead to a markedly increase in the productivity of the workers, doctors or nurses.

The present invention provides a novel type of low alcohol, quick-drying, gel-type disinfectant composition, i.e. a water-based disinfectant composition, comprising one or more anti-microbicidal ingredients, 0–30% of an alcohol, a thickening agent, an emulsifier, and water.

The present invention also provides the use of such a composition as a hand disinfectant.

The present invention furthermore provides a gel-type carrier system comprising 1–20% of an alcohol, 0.2–1.6% of an acrylic acid copolymer as a thickening agent, 0.1–3.2% of an emulsifier, optionally 0.2–0.6% of a basic component and the balance of water.

Such novel carrier systems may be useful in various fields, e.g. in the field of paints and in skin care products.

DETAILED DESCRIPTION OF THE INVENTION

Figure 1:
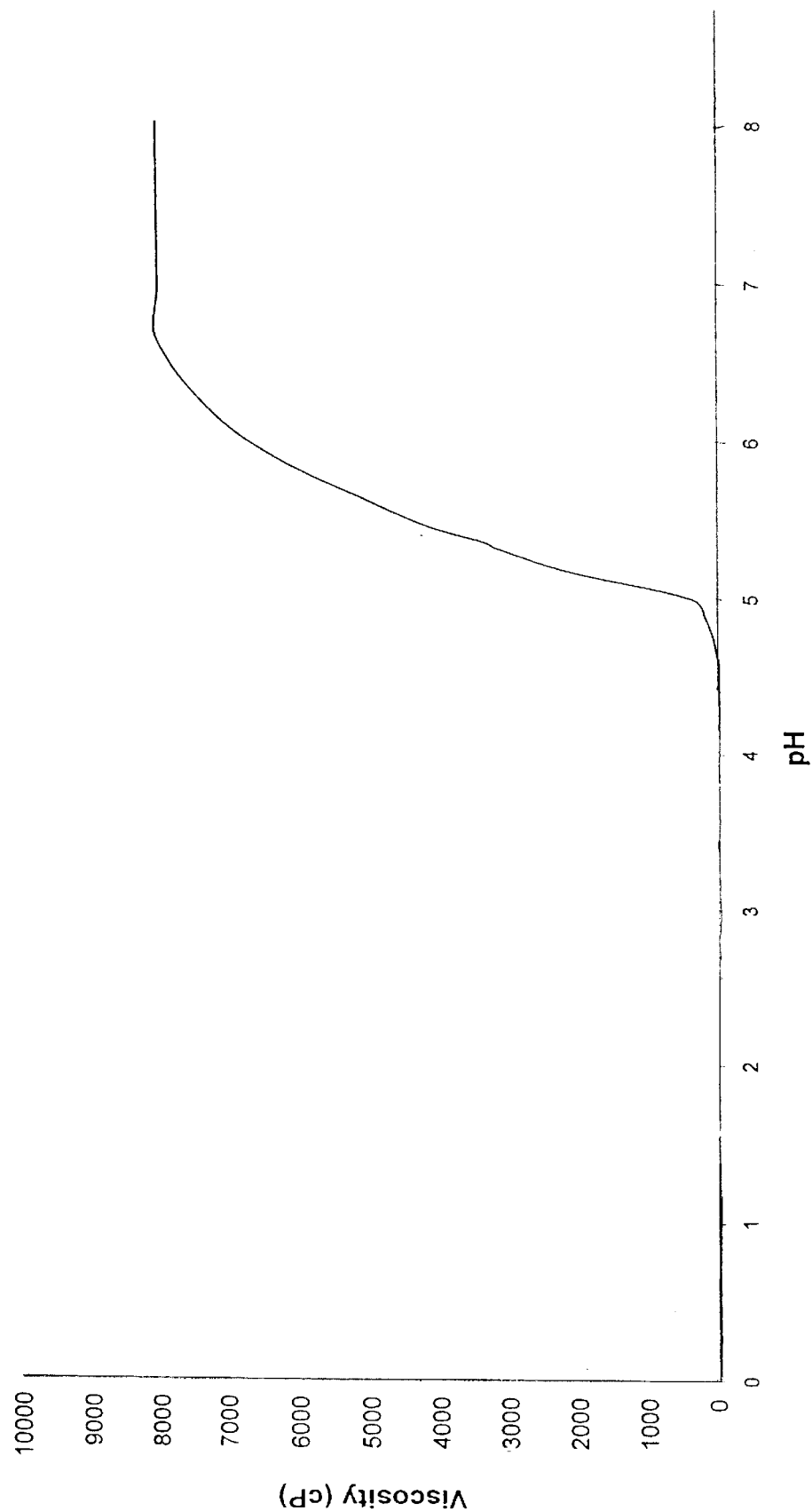
FIG. 1 is a graphical representation that demonstrates gel viscosity pH dependence.

All relative amounts stated as "%" refer to the weight to weight percentage.

Relevant anti-microbicidal ingredient to be used within the present invention are ingredients which effectively are able to kill or inactivate micro-organisms so as to reduce the risk of cross-contamination. Virtually any anti-microbicidal ingredient can be used taking into consideration the toxicity (towards animals) of the anti-microbicidal ingredient. Illustrative examples of anti-microbicidal ingredients are triclosan (Irgasan® DP-300 (Ciba)), phenoxyethanol, chlorhexidine gluconat, povidone-iodine, iodophor, benzalkonium chloride, benzethonium chloride, and cresol.

The before-mentioned anti-microbicidal ingredients may be used alone or in combination. Often the combination of two or more anti-microbicidal ingredients is desirable in order to obtain a broad-spectrum disinfectant composition.

The actual amount of the anti-microbicidal ingredient used will of course depend on the efficiency thereof. However, typically, the anti-microbicidal ingredient is used in an amount of 0.05–5.0%, such as 0.1–3.8%, preferably 0.15–3.0%.

The alcohol used with in the present context is typically a $C_{1-4}$ alcohol, such as ethanol and iso-propanol, or mixtures thereof. Preferably the alcohol is ethanol. The content of the alcohol in the disinfectant composition is 0–30%, such as 0–25%, preferably 1–20%, such as 2–15%, in particular 3–12% or 5–15%.

The thickening agent which constitutes a crucial component in the disinfectant composition according to the present invention is preferably selected from acrylic acid copolymers, methacrylic acid copolymers, sodium carboxy cellulose, hydroxyethyl cellulose, and hydroxypropyl cellulose, or the thickening agent is a mixture of the before-mentioned components. More preferably the thickening agent is a polymeric component having pendant carboxylic acid groups such as acrylic or methacrylic acid polymers.

Illustrative examples of commercially available thickening agents are Carbopol® (e.g.

Carbopol ULTREZ 10, Carbopol® EZ 2, Carbopol® ETD 2001, Carbopol® ETD 2020, Carbopol® ETD 2050, Carbopol® 934, Carbopol® 2984, Carbopol® 940 and Carbopol® 1342) (B.F. Goodrich), Natrosol® (supplied from Brøste, Denmark), Satiaxane® (supplied from Superfos, Denmark), Celacol® (supplied from Superfos, Denmark), Courlose® (supplied from Superfos, Denmark), and Cekol® (supplied from Superfos, Denmark).

The content of the thickening agent is typically 0.05–2.5%, such as 0.1–1.6%, preferably 0.15–1.4%, such as 0.2–1.2% or 0.15–0.5%.

The disinfectant composition according to the present invention also comprises one or more emulsifiers. The emulsifiers suitably can be selected among a number of commercially available emulsifiers, preferably from fatty alcohol-polyglycol ethers (fatty alcohol ethoxylates) and mixtures thereof.

Illustrative examples of commercially available emulsifiers are Synperonic® (supplied from Superfos, Denmark) and Cremophor® (supplied from BASF, Denmark).

The content of the emulsifier in the disinfectant composition is typically 0.05–5%, such as 0.1–3.2%, preferably 0.2–2.0%.

The disinfectant according to the present invention preferably further includes a rewetting agent. The rewetting agent is preferably selected from fatty acid polydiethanolamides, betaine, lanolin, paraffin oil, coco-fatty acid diethanolamide, coco-fatty acid monoethanolamide, and glycerin, in particular glycerin.

The content of the rewetting agent of course depends on the need for rewetting or remoisturising of the hand or skin (which again depend on the frequency of use), but the content is typically (in the cases where a rewetting agent is used) 0.1–5.0%, such as 0.5–4.5% or 1.0–4.0%, preferably 1.5–3.0%.

The disinfectant composition may further comprise one or more additives, e.g. perfumes, colorants, preservatives, and pH adjusting agents (such as basis compounds). The total content of such additives (when present) is typically 0.01–2.0%, such as 0.05–1.5%, preferably 0.1–1.0% or 0.2–0.7%.

By the use of the unique combination of water, alcohol, a thickening agent and an emulsifier described herein, it is possible to obtain a disinfectant composition which fulfils the requirements with regard to drying time and lack of irritation of the skin and at the same time has a suitable viscosity. In order to ease the use and application of the composition, it is believed that the composition should have a viscosity in the range of 1,000–150,000 centipoises, such as in the range of 1,500–50,000 centipoises, preferably in the range of 3,000–30,000 centipoises, more preferably in the range of 3,000–15,000. Such suitable viscosity can be obtained by adjusting the amount of the thickening agent and/or by adjusting the pH of the composition. This is especially relevant where the thickening agent is an acrylic or methacrylic acid polymer as the gradual salt formation by addition of a base will alter the viscosity. Examples 3 and 4 illustrates this phenomenon.

As the disinfectant composition should be applied to the hands or the skin of the user, the composition should preferably have a pH in the range of 4.6–7.3, such as in the range of 5.0–6.5, preferably in the range of 5.0–6.0 or 5.2–6.0.

The pH of the disinfectant may be adjusted with a suitable basic compound (as the thickening agent typically is a slightly acidic component, e.g. a polymeric component having pendant carboxylic acid groups such as acrylic or methacrylic acid polymers), preferably a fatty amine or triethanolamine. The amount of basis component used is typically constituting 0.05–1.0% such as 0.2–0.6% of the total amount of additives. (basic compounds are to be considered as additives, cf. above.) The adjustment of the pH is typically performed by titration to the desired pH value as described in the Examples, thus, the basic component is often considered as a mandatory component where the thickening agent is a polymeric component having pendant carboxylic acid groups.

An illustrative example of a commercially available basic compounds is Tela 99/90 (supplied from Superfos, Denmark)

A suitable viscosity is often a function of the pH of the disinfectant (typically adjusted by use of a basic compound, cf. above) and the content of the thickening agent, thus, in the case where the pH of disinfectant is in the range of 4.6–5.5, the content of the thickening agent is preferably in the range of 0.6–1.6%, whereas the content of the thickening agent preferably in the range of 0.1–1.0% when the pH of disinfectant is in the range of 5.5–7.3.

One of the unique properties of the disinfectant composition according to the invention is that it, when applied to the hands of the user, is "drying fast". Fast drying is either obtained by rapid absorption into the skin or by evaporation of the "volatile" components, or (most likely) a combination of these processes. For practical use, the composition according to the invention has a drying time of at the most 60 sec. when tested in the "Hand rubbing test", preferably at the most 45 sec. or at the most 30 sec.

Another important feature of the composition of the present invention is it's ability to "melt" when contacted with the skin of the user. This facilitates the even application of the composition on the skin. The compositions have a desirable high viscosity when stored and applied, by when applied to the skin of the user, the viscosity tends to decrease more than would be expected due to contact with salty skin moisture. It is believed that this phenomenon is at least partially responsible for the excellent "drying" properties of the compositions according to the present invention.

In a preferred embodiment, the present invention relates to a disinfectant composition comprising 0.05–5.0% of one or more anti-microbicidal ingredients, 1–20% of an alcohol, 0.05–2.5% of a thickening agent, 0.05–5.0% of an emulsifier, 0.0–5.0% of a rewetting agent, 0.0–2.0% of one or more additives, and the balance of water or substantially the balance of water. Preferably the viscosity is in the range of 5,000–50,000 centipoises, more preferably in the range of 3,000–15,000 centipoises.

In a more preferred embodiment, the present invention relates to a composition comprising 0.05–5.0% of one or more anti-microbicidal ingredients, 1–20% of ethanol, 0.05–2.5% of an acrylic acid copolymer as a thickening agent, 0.05–5.0% of a fatty acid alcohol-polyglycol ether as an emulsifier, 0.5–5.0% of glycerin, 0.01–2.0% of one or more additives including 0.05–1.0% of a basic compound, and the balance of water or substantially the balance of water. Preferably the viscosity is in the range of 5,000–50,000 centipoises, more preferably 3,000–15,000 centipoises.

In an even more preferred embodiment, the present invention relates to a composition comprising 0.05–5.0% of one or more anti-microbicidal ingredients, 2–15% of ethanol, 0.2–1.2% of an acrylic acid copolymer as a thickening agent, 0.2–2.0% of a fatty acid alcohol-polyglycol ether as an emulsifier, 1.0–4.0% of glycerin, 0.2–0.7% of one or more additives including 0.05–1.0% of a basic compound, and substantially the balance of water.

For these specific compostions, the viscosity is preferably in the range of 3,000–15,000 and the pH value is preferably in the range of 5.0–6.5.

In view of the unique novel disinfectant composition, it is believed that the combination of alcohol, water, the interesting combination of the specific preferred thickening agent and an emulsifier, will be equally interesting for other types of formulations where similar properties (short drying time and suitable viscosity) are desirable. Thus, the present invention also relates to a gel-type carrier system comprising 1–20% of an alcohol, 0.2–1.6% of an acrylic acid copolymer as a thickening agent, 0.1–3.2% of an emulsifier, optionally 0.2–0.6% of a basic component and the balance of water. Preferably, the gel-type carrier system has a viscosity in the range of 1,500–150,000 centipoises, more preferably in the range of 3,000–15,000. The preferred specific embodiments with respect to content and quality of the individual components as well as possible further components mentioned above for the disinfectant composition also applies for the gel-type carrier system, with the necessary modifications.

Such as carrier system may have a broad range of applications, e.g. in paints and in skin care products such as in after shave lotions.

EXAMPLES

General Preparation Method

The anti-microbicidal ingredients), the emulsifier, and any wetting agent were dissolved in the alcohol. The thickening agent (typically in the form of a powder) was mixed with water. The mixture was allowed to stand until the powder was soaked with water. The alcoholic solution was then added to the mixture. pH was optionally adjusted by slowly adding a basis component under constant stirring until the desired pH value was obtained. The pH values were determined using a Knick pH-meter Model 911 (X)pH.

Example 1

Various gel-type compositions (without anti-microbicidal agents) (see Table I) were prepared as described above and were tested with respect to three different criteria, i.e. viscosity, drying time, and user rating in order to determine the optimal mutual relationship between the four important ingredients. The compositions consisted of five ingredient (composition 16 however only four ingredients): Ethanol (ethanol, 99.9%), Carbopol (Carbopol ULTREZ-10, B.F. Goodrich), Synperonic (Synperonic 91/8T (85%), Superfos, Denmark), water, and Glycerin (Glycerin (99.7%)). The pH was adjusted to around 5.2 with triethanolamine.

TABLE I

|  | Ethanol (% (w/w)) | Carbopol (%(w/w)) | Synperonic (%(w/w)) | Water (%(w/w)) | Glycerin (%(w/w)) |
|---|---|---|---|---|---|
| 1 | 5.9 | 0.9 | 2.0 | 88.7 | 2.5 |
| 2 | 31.1 | 0.9 | 2.0 | 63.5 | 2.5 |
| 3 | 18.5 | 0.2 | 2.0 | 76.8 | 2.5 |
| 4 | 18.5 | 1.6 | 2.0 | 75.4 | 2.5 |
| 5 | 18.5 | 0.9 | 0 | 78.1 | 2.5 |
| 6 | 18.5 | 0.9 | 3.9 | 74.2 | 2.6 |
| 7 | 11.0 | 0.5 | 0.8 | 85.2 | 2.5 |
| 8 | 26.0 | 0.5 | 0.8 | 70.2 | 2.5 |
| 9 | 11.0 | 1.3 | 0.8 | 84.4 | 2.5 |
| 10 | 26.0 | 1.3 | 0.8 | 69.4 | 2.5 |
| 11 | 11.0 | 0.5 | 3.1 | 82.9 | 2.5 |
| 12 | 26.0 | 0.5 | 3.1 | 67.9 | 2.5 |
| 13 | 11.0 | 1.3 | 3.1 | 82.1 | 2.5 |
| 14 | 26.0 | 1.3 | 3.1 | 67.1 | 2.5 |

TABLE I-continued

|  | Ethanol (% (w/w)) | Carbopol (%(w/w)) | Synperonic (%(w/w)) | Water (%(w/w)) | Glycerin (%(w/w)) |
|---|---|---|---|---|---|
| 15 | 18.5 | 0.9 | 2.0 | 76.1 | 2.5 |
| 16 | 10.0 | 0.4 | 1.0 | 88.6 | 0 |

Hand Rubbing Test—Evaluation of the Drying Time

Before starting the evaluating, the hands of the testing person must be washed in warm water and dried in towels at least 3 min. before adding the test composition to the palm of the hands. The hands must have a temperature of approximately 30° C. 1.5 ml of the test compositionis rubbed into the hands according to the procedure described in the European Standard EN 1500. After 30 sec. from application of the test position, the left hand (one hand) is pressed on a piece of standard copier paper (A5, 80 g paper). If the paper sticks to the hand when the hand is lifted, the hand are evaluated "Not Dry after 30 sec". Otherwise the hands are evaluated "Dry after 30 sec". In the first case ("Not Dry after 30 sec."), the pressure test is repeated with the right hand (the other hand) on a similar piece of paper after 45 sec., and if necessary again on after 60 sec. (left hand again), following the same evaluation procedure. If the hands are "Not Dry after 60 sec.", the test is not carried on further.

The result of the Hand rubbing test for compositions 1–16 are shown in Table II.

TABLE II

|  | Drying time (sec.) |
|---|---|
| 1 | 45 |
| 2 | 45 |
| 3 | 30 |
| 4 | 45 |
| 5 | 60 |
| 6 | 45 |
| 7 | 45 |
| 8 | 30 |
| 9 | 60 |
| 10 | 60 |
| 11 | 45 |
| 12 | 30 |
| 13 | 60 |
| 14 | 60 |
| 15 | 45 |
| 16 | 45 |

Viscosity

The viscosity of compositions 1–16 was measured on a Brookfield viscometer equipped with a T-spindle type D, run at a speed of 6 rpm. The measured viscosities (both the viscosity relative to water and the absolute viscosity) are shown in Table III.

TABLE III

|  | Viscosity (relative %) | Viscosity centipoises |
|---|---|---|
| 1 | 12.0 | 80,000 |
| 2 | 14.0 | 94,000 |
| 3 | 0.2 | 1,300 |
| 4 | 24.5 | 160,000 |
| 5 | 24.0 | 162,000 |
| 6 | 10.2 | 68,000 |
| 7 | 9.2 | 58,000 |
| 8 | 7.2 | 48,000 |
| 9 | 15.1 | 100,000 |
| 10 | 25.5 | 170,000 |
| 11 | 4.7 | 32,000 |

TABLE III-continued

|    | Viscosity (relative %) | Viscosity centipoises |
|----|------------------------|------------------------|
| 12 | 0.4                    | 2,700                  |
| 13 | 21.8                   | 142,000                |
| 14 | 25.0                   | 172,000                |
| 15 | 14.6                   | 98,000                 |
| 16 | 5.5                    | 39,000                 |

Based on the above results, it was concluded that the content of the thickening agent (Carbopol) was quite sensitive, whereas the concentration of the emulsifier (Synperonic) was less critical. Reference example 16 illustrated that the rewetting agent glycerin had no substantial impact on the viscosity and the drying time.

Example 2

A composition comprising 2.4% of two anti-microbicidal ingredients (2.0% of phenoxyethanol and 0.4% of Irgasan® DP-300), 10% ethanol, 0.35% of a thickening agent (Carbopol® ULTREZ-10), 1.0% of an emulsifier (Synperonic® 91/8T 85%), 2.5% of a rewetting agent (Glycerin), 0.15% of a basic compound (Tela 99/90) (to pH 5.5±0.1) and the balance (83.75%) of water was prepared as described above. The viscosity of the composition was 15,000 centipoise and the drying time was 45 sec.

Example 3

The viscosity of a gel as a function of the pH was measured. A composition corresponding to the one described in example 2 was prepared. Before adjusting the pH to obtain the proper viscosity the pH, was measured. While slowly increasing the pH by adding triethanolamine coherent values of pH and viscosity were measured. These results are shown in table IV. The test was performed at 21° C. The viscosity was measured on a Brookfield Viscometer equipped with a T-spindle type D run at a speed of 20 RPM. The pH was measured at a Knick pH-meter Model 911 (X)pH. From FIG. 1 it appears that the viscosity of a gel prepared by using Carbopol is dependent of the pH of the gel. The viscosity rises significantly around pH 5.2–5.7.

TABLE IV

|       | pH   | Viscosity (relative %) | Viscosity centipoises |
|-------|------|------------------------|------------------------|
| Start | 4.50 | 0                      | 0                      |
|       | 4.88 | 0.2                    | 200                    |
|       | 5.00 | 0.4                    | 400                    |
|       | 5.16 | 2.1                    | 2100                   |
|       | 5.31 | 3.2                    | 3200                   |
|       | 5.35 | 3.4                    | 3400                   |
| End   | 6.57 | 8.1                    | 8100                   |

Example 4

Figure 2:
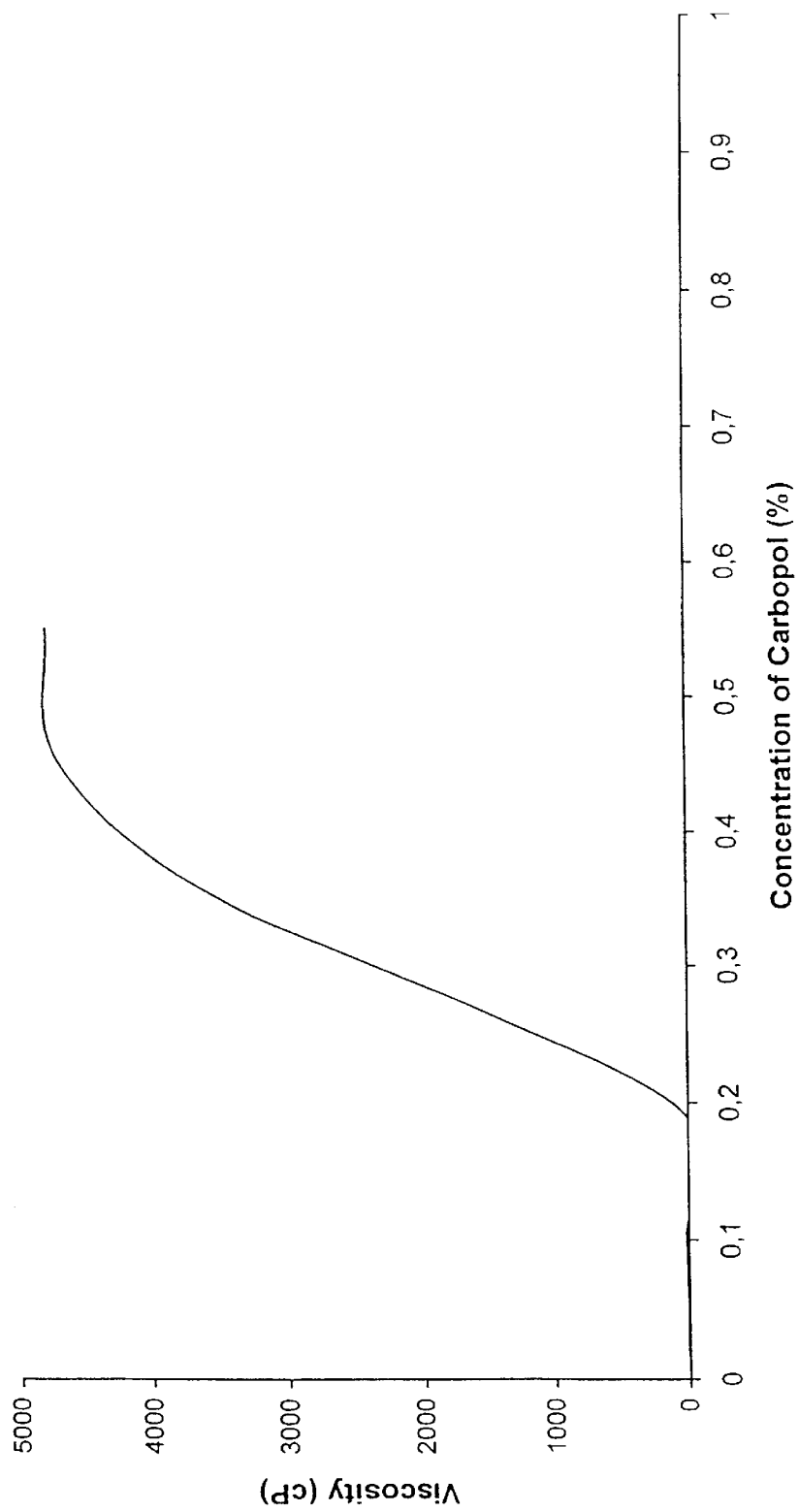
FIG. 2 is a graphical representation that demonstrates gel viscosity increase within a narrow concentration of thickening agent.

The viscosity of a gel as a function of the concentration of thickening agent was measured. The various compositions were prepared as described in example 2. The only variable ingredient was the thickening agent and water which is used to balance the solution. The pH was adjusted to a constant value of 5.5 by adding triethanolamine. The results appear from table V. The test was performed at 21° C. The viscosity was measured on a Brookfield Viscometer equipped with a T-spindle type D run at a speed of 100 RPM. The pH was measured at a Knick pH-meter Model 911 (X)pH. FIG. 2 shows that the viscosity of a gel increases very much within a narrow concentration of the thickening agent.

TABLE V

|   | Concentration of Carbopol | Viscosity (relative %) | Viscosity Centipoise |
|---|---------------------------|------------------------|----------------------|
| 1 | 0.10                      | 0.02                   | 20                   |
| 2 | 0.20                      | 0.60                   | 120                  |
| 3 | 0.35                      | 10.5                   | 3500                 |
| 4 | 0.45                      | 14.0                   | 4700                 |

What is claimed is:

1. A water-based, quick-drying, gel disinfectant composition having a pH in the range of 5.0–6.5, said composition comprising 0.05–5.0% of one or more anti-microbial ingredients, 2–15% of a $C_{1-4}$-alcohol, 0.15–1.2% of a thickening agent, 0.05–5.0% of a fatty alcohol-polyglycol ether as an emulsifier, 0.0–5.0% of a rewetting agent, and substantially the balance of water, said composition having a drying time of at the most 45 sec. when tested by a "Hand rubbing test" using the following testing procedure:

the test person washes his or her hands in warm water and dries the hands in a towel so as to provide clean hands having a temperature of approximately 30 C. at least 3 minutes prior to rubbing 1.5 milliliters of the test composition into the palms of the hands, then 45 seconds after rubbing the test composition into the palms of the hands, one hand is pressed onto a piece of standard copier paper and then lifted, whereupon if the paper sticks to the hand when the hand is lifted, the hands are evaluated as "not dry after 45 seconds" while if the paper does not stick to the hand when the hand is lifted, the hands are evaluated as "dry at 45 seconds or less than 45 seconds".

2. The composition of claim 1, wherein the thickening agent is selected from acrylic acid copolymers, methacrylic acid copolymers, sodium carboxy cellulose, hydroxyethyl cellulose, and hydroxypropyl cellulose.

3. The composition of claim 1, wherein a basic compound in an amount of 0.05–1.0% brings the pH of said composition to 5.0–6.5.

4. The composition of claim 1, wherein the content of the thickening agent is in the range of 0.15–0.5%.

5. The composition of claim 1 which has a viscosity in the range of 1,500–50,000 centipoises.

6. The composition of claim 1, wherein said $C_{1-4}$ alcohol is ethanol, said thickening agent is an acrylic acid copolymer, said re-wetting agent is 0.5–5.0% of glycerin, and said composition further comprises 0.01–1.0% of one or more additives including 0.05–1.0% of a basic compound.

7. The composition of claim 6, wherein said acrylic acid copolymer is in an amount of 0.15–0.5%, said fatty alcohol-polyglycol ether is in an amount of 0.2–2.0% and said one or more additives is in an amount of 0.2–0.7%.

8. A method of disinfecting hands, comprising the step of utilizing a composition of claim 1 as a hand disinfectant.

9. A method of disinfecting hands, comprising the step of utilizing a composition of claim 7 as a hand disinfectant.

10. The composition according to claim 1, having a drying time of at most 30 seconds.

* * * * *